US012721918B2

(12) United States Patent
Parias et al.

(10) Patent No.: US 12,721,918 B2
(45) Date of Patent: Sep. 1, 2026

(54) NON-THERMAL PLASMA CLEANING DEVICE AND CLEANING METHOD

(71) Applicants: AURORA, Rouen (FR); UNIVERSITE DE REIMS CHAMPAGNE-ARDENNE, Reims (FR)

(72) Inventors: Thomas Parias, Rouen (FR); Florian Le Bras, Rouen (FR); Marie-Paule Gellé, Reims (FR)

(73) Assignees: AURORA, Rouen (FR); UNIVERSITE DE REIMS CHAMPAGNE-ARDENNE, Reims (FR)

( * ) Notice: Subject to any disclaimer, the term of this patent is extended or adjusted under 35 U.S.C. 154(b) by 1076 days.

(21) Appl. No.: 17/871,122

(22) Filed: Jul. 22, 2022

(65) Prior Publication Data

US 2024/0024527 A1 Jan. 25, 2024

(51) Int. Cl.
*A61L 2/14* (2006.01)

(52) U.S. Cl.
CPC ............. *A61L 2/14* (2013.01); *A61L 2202/11* (2013.01); *A61L 2202/122* (2013.01); *A61L 2202/15* (2013.01)

(58) Field of Classification Search
CPC .. A61L 2/14; A61L 2202/11; A61L 2202/122; A61L 2202/15; A61L 2202/16; A61L 2202/14; A61L 2/22; A61L 2/186; A61L 2/202; A61L 2/24; A61L 2202/13; A61L 2/20; A61L 2101/20; A61L 2103/15; A23B 7/015; A23B 2/50; H01J 37/32; H05H 1/466; H05H 1/46; B01D 53/56; B01D 2251/104; B01D 2251/108; B01D 2257/404; A61M 5/001
See application file for complete search history.

(56) References Cited

U.S. PATENT DOCUMENTS

2017/0304476 A1* 10/2017 Taggart ..................... A61L 2/22
2021/0220500 A1* 7/2021 Lam ....................... A23B 7/015
2022/0001056 A1 1/2022 Truica-Marasescu

FOREIGN PATENT DOCUMENTS

EP 2618851 A1 7/2013
JP 3813586 B2 8/2006

OTHER PUBLICATIONS

European Search Report issued on Jan. 5, 2023, in corresponding European Application No. 22306097, 6 pages.

(Continued)

*Primary Examiner* — Xiuyu Tai
(74) *Attorney, Agent, or Firm* — Maier & Maier, PLLC

(57) ABSTRACT

A non-thermal plasma cleaning device including: an enclosure including an input port for fluid connection with a gas supply; a radio-wave source; a controller configured to successively perform, during a cleaning step, at least two, preferably at least three, non-thermal plasma generation cycles each including: controlling the radio-wave source to be in an active state during a first predetermined duration to generating a non-thermal plasma in the enclosure; and controlling the radio-wave source to be in an inactive state during a second predetermined duration, the input port being in an open state at least during the second predetermined duration.

11 Claims, 4 Drawing Sheets

(56) References Cited

OTHER PUBLICATIONS

Fiebrandt et al., "From patent to product? 50 years of low-pressure plasma sterilization", Plasma Process Polymers, 2018, 17 pages.
International Preliminary Report on Patentability issued Nov. 6, 2024, in corresponding International Application No. PCT/EP2023/068900, 8 pages.
Lerouge et al., "Effect of Gas Composition on Spore Mortality and Etching During Low-Pressure Plasma Sterilization", J Biomed Mater Res, John Wiley & Sons, Inc., vol. 51, Jul. 2000, 8 pages.

* cited by examiner

NON-THERMAL PLASMA CLEANING DEVICE AND CLEANING METHOD

FIELD

The invention concerns a non-thermal plasma cleaning device of the type including:

- an enclosure for receiving at least one object to be cleaned, the enclosure including an input port for fluidly connecting the enclosure to a gas supply;
- a radio-wave source having an active state wherein the radio-wave source outputs an electromagnetic wave and an inactive state wherein the radio-wave source does not output the electromagnetic wave, the electromagnetic wave having a frequency in the radio wave range or the microwave range, the radio-wave source being coupled to the enclosure so that, in the active state, the electromagnetic wave propagates in the enclosure.

The invention also concerns a cleaning assembly comprising such non-thermal plasma cleaning device, as well as a cleaning method.

The invention relates to the field of cleaning using plasma, especially the cleaning of medical supplies and equipment.

BACKGROUND

It is known to use plasma to sterilize an object. For instance, document EP 2 618 851 A1 discloses a sterilization device using non-thermal plasma for the sterilization of an object, such as a medical device, namely an implant.

By "non-thermal plasma" (also referred to as "cold plasma" or "non-equilibrium plasma"), it is meant, in the context of the present invention, a plasma wherein the electrons and the heavy species (ions and neutrals) are not in thermodynamic equilibrium with each other. In such a plasma, the temperature of the electrons (up to several tens of thousands kelvin) is much higher than the temperature of the heavy species which is typically kept around room temperature—ie −50° C. by tuning the proper parameters of the plasma generation setup. The temperature to which items such as medical devices placed in such an unbalanced plasma phase are exposed, is the temperature of the heavy species hence around room temperature.

The aforementioned sterilization device includes a sealed chamber for receiving an object to be sterilized, a vacuum pump for subjecting the chamber to a secondary vacuum, as well as an electron cyclotron resonance generator for generating micro-waves and a magnetic field in the chamber. Due to the electromagnetic fields output by the generator, a non-thermal plasma is ignited in the chamber, thereby resulting in a sterilization of the object placed in the chamber.

However, such device is not fully satisfactory.

Indeed, it results from Regulation (EU) 2017/745 that a sterilization is considered effective if the number of contaminants has been divided by at least $10^6$. Nevertheless, the duration required to achieve such reduction using the aforementioned device is unacceptably long.

For a purpose of illustration, FIG. 1 shows an evolution over time of the number of A) gram-negative bacteria (*Pseudomonas aeruginosa*), B) gram-positive bacteria (*Staphylococcus aureus*) and C) spores (*Bacillus subtilis* spores), during a non-thermal plasma cleaning method implemented with the aforementioned device in vacuum, oxygen, argon and nitrogen for the gram-negative and gram-positive bacteria, and in vacuum and oxygen for the spores.

Indeed, as can be seen from FIG. 1, the duration required to achieve such reduction using the aforementioned device is around one hour for gram-negative bacteria (*Pseudomonas aeruginosa*, curve A), two hours for gram-positive bacteria (*Staphylococcus aureus*, curve B), which is unacceptably long for a commercial use. Moreover, it has been shown that, using the aforementioned device, the reduction in the number of spores (*Bacillus subtilis* spores, curve C) never reaches a factor of $10^6$, even after two hours.

A purpose of the invention is to provide a cleaning device that is more time-efficient than known plasma-based cleaning devices.

SUMMARY

To this end, the present invention is a non-thermal plasma cleaning device of the aforementioned type, wherein the non-thermal plasma cleaning device further includes:

- a controller configured to successively perform, during a cleaning step, at least two, preferably at least three, non-thermal plasma generation cycles, each non-thermal plasma generation cycle comprising:
  - controlling the radio-wave source to be in the active state during a first predetermined duration, thereby generating a non-thermal plasma in the enclosure; and
  - following the first predetermined duration, controlling the radio-wave source to be in the inactive state during a second predetermined duration, the input port being in an open state at least during the second predetermined duration to allow a flow of gas into the enclosure, each of the first predetermined duration and the second predetermined duration being strictly greater than zero.

Indeed, the inventors have discovered that the reaction kinetics involved in the generation of the plasma are such that the chemical species that contribute the most to the degradation of undesired chemicals and/or pathogens (i.e., radicals and/or molecules in an excited state), hereinafter called "reactants of interest", are present in a very small minority, in the steady-state, compared to other less reactive species. On the contrary, the fraction of the reactants of interest is significantly higher in the transient state. The transient state covers the first minutes after the plasma is ignited during which the concentration of reactive species are rapidly evolving. It differs from the steady state observed several minutes after the plasma phase is established and during which the reactive species concentration are stable.

Consequently, by performing a plurality of such non-thermal plasma generation cycles hereby defined as turning on and off a non-thermal plasma during two defined timings, and by allowing a flow of gas from the gas supply to the enclosure at least during the second duration of each non-thermal plasma generation cycle, the reactants of interest that appear when the plasma is ignited are regenerated.

As a result, the invention provides a cleaning that is far more efficient than that achieved to known non-thermal plasma cleaning devices.

According to other advantageous aspects of the invention, the non-thermal plasma cleaning device includes one or more of the following features, taken alone or in any possible combination.

The non-thermal plasma cleaning device may further include a pump fluidly connected to the enclosure, the controller being configured to operate the pump so that, during at least one non-thermal plasma generation cycle, a pressure within the enclosure is below a predetermined threshold.

The predetermined threshold may be lower than 4000 Pa, preferably comprised between $0.5 \times 10^{-6}$ Pa and 400 Pa.

The radio-wave source may be configured so that the electromagnetic wave has a frequency:

- comprised in an interval ranging from 30 kHz to 300 MHz, especially 30 kHz to 30 MHz, preferably in at least one interval:
  - ranging from 6.765 MHz to 6.795 MHz;
  - ranging from 13.553 MHz to 13.567 MHz; and/or
  - ranging from 26.957 MHz to 27.283 MHz; and/or
- comprised between 1 GHz and 5 GHz, preferably between 2 GHz and 3 GHz, for instance equal to 2.45 GHz.

The first predetermined duration may be less than 5 minutes, preferably less than 3 minutes, advantageously less than 2 minutes, for instance less than 1 minute.

The second predetermined duration may be less than 5 minutes, preferably less than 3 minutes, advantageously less than 2 minutes, for instance less than 30 seconds.

The controller may be configured to successively perform, during the cleaning step, at least five non-thermal plasma generation cycles.

The input port may be in an open state at least during the second predetermined duration to allow a flow of gas from the gas supply to the enclosure.

The non-thermal plasma cleaning device may further include at least one sensor configured to output a sensing signal representative of a temperature within the enclosure, the controller being further configured to control the radio-wave source to be in the inactive state if the temperature determined based on the sensing signal is greater than a predetermined maximum value.

The invention also relates to a cleaning assembly including a gas supply and a non-thermal plasma cleaning device as defined previously, the gas supply being fluidly connected to the input port of the enclosure to provide gas to the enclosure of the non-thermal plasma cleaning device.

According to other advantageous aspects of the invention, the cleaning assembly includes one or more of the following features, taken alone or in any possible combination.

The gas may be air, or include at least one of: nitrogen, oxygen, argon and helium.

The gas supply and the input port of the enclosure may be sized so that, during the second predetermined duration, a predetermined amount of gas is injected in the enclosure.

The invention also relates to a non-thermal plasma cleaning method including the steps:

- arranging at least one object to be cleaned in an enclosure; and
- successively performing at least two, preferably at least three, non-thermal plasma generation cycles, each non-thermal plasma generation cycle comprising:
  - controlling a radio-wave source to be in an active state during a first predetermined duration, thereby generating a non-thermal plasma in the enclosure; and
  - following the first predetermined duration, controlling the radio-wave source to be in an inactive state during a second predetermined duration, a flow of gas being injected in the enclosure at least during the second predetermined duration, wherein, in the active state, the radio-wave source outputs an electromagnetic wave, and in the inactive state, the radio-wave source does not output the electromagnetic wave, the electromagnetic wave having a frequency in the radio wave range or the microwave range, the radio-wave source being coupled to the enclosure so that, in the active state, the electromagnetic wave propagates in the enclosure, each of the first predetermined duration and the second predetermined duration being strictly greater than zero.

According to other advantageous aspect of the invention, the cleaning method further includes, before at least one non-thermal plasma generation cycle, bringing a pressure within the enclosure below a predetermined threshold.

BRIEF DESCRIPTION OF THE DRAWINGS

The invention will be better understood with the attached figures, in which.

DETAILED DESCRIPTION

Figure 1:
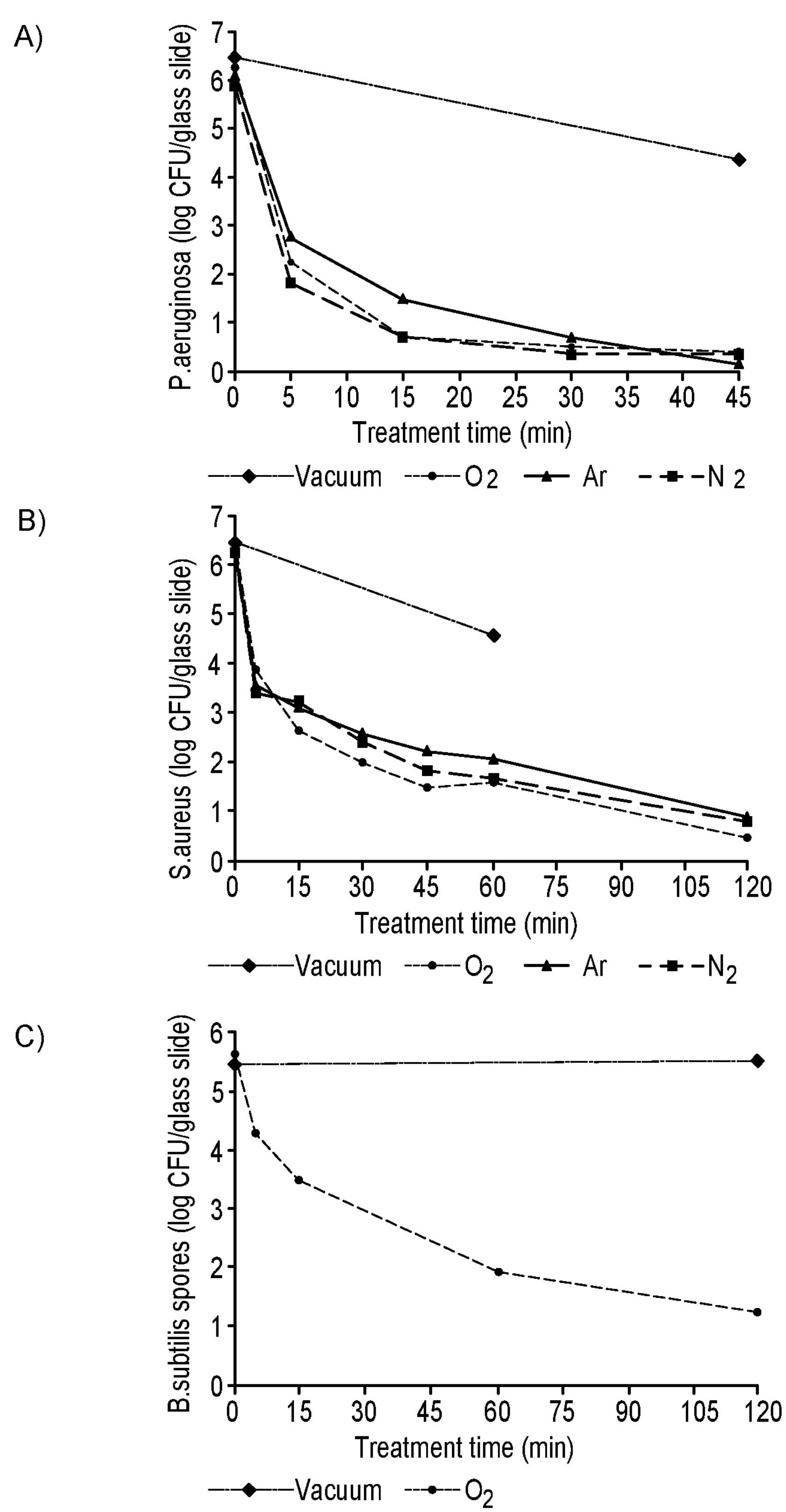
FIG. 1 is a graph showing the evolution, as a function of time, of the number (in logarithmic scale) of contaminants on a surface cleaned using a known non-thermal plasma sterilization device.
Figure 2:
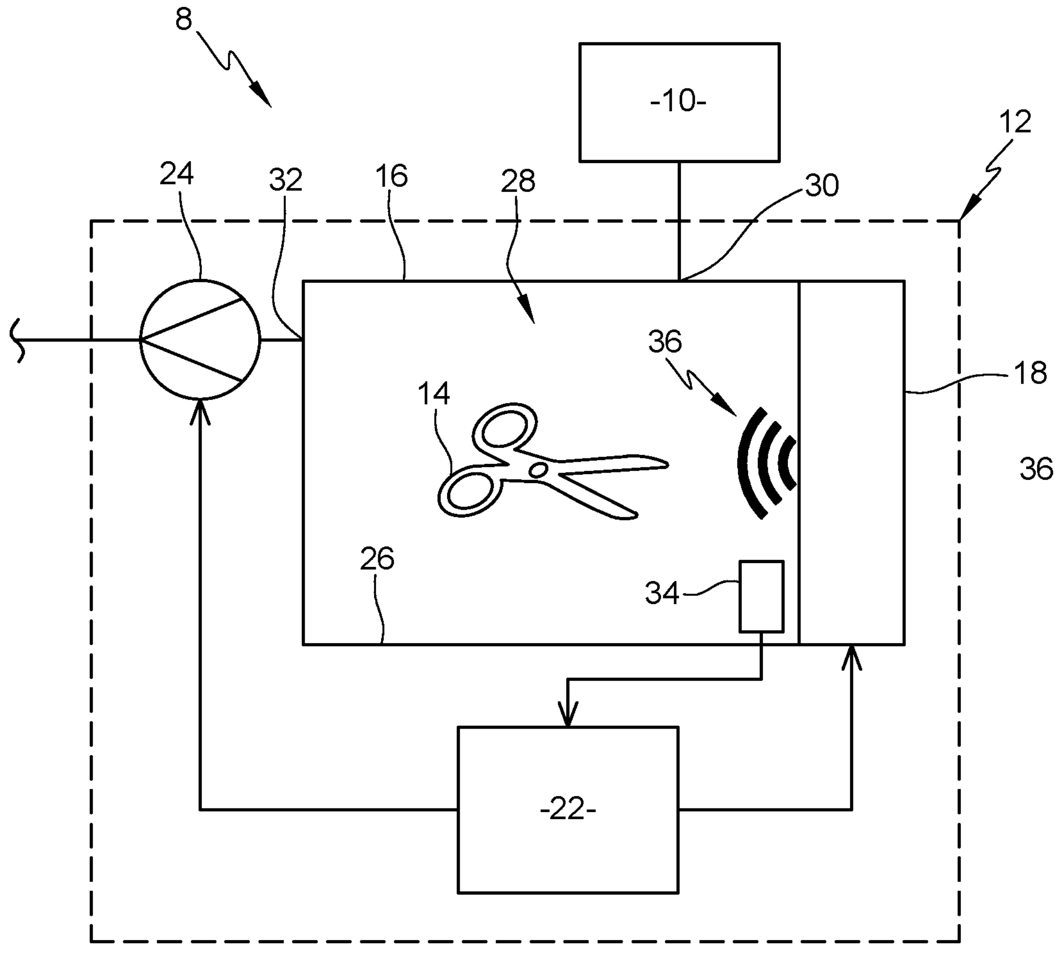
FIG. 2 is a schematic representation of a first embodiment of a cleaning assembly according to the invention.

A cleaning assembly 8 according to the invention is shown on FIG. 2.

By "cleaning", it is meant, in the context of the present invention, the sterilization, the disinfection, and/or the decontamination of an object or a surface.

By "sterilization", it is meant, in the context of the present invention, the total or quasi-total removal of the biological load (bacteria, spores, viruses or proteins). More precisely, according to norm ISO 14937, sterilizing an object corresponds to dividing the biological load thereon by a factor of at least $10^6$. In other words, a medical device is considered to be sterilized when the probability of contamination is less than one in a million.

By "disinfection", it is meant, in the context of the present invention, an incomplete removal of the biological load. More precisely, disinfecting an object corresponds to dividing the biological load thereon by $10^4$ to $10^6$. In other words, a medical device is considered to be disinfected when the probability of contamination is comprised between one in ten thousand and one in a million.

By "decontamination", it is meant, in the context of the present invention, a reduction (i.e., division) of the biological load on an object by $10^4$ or less. Decontamination may also refer to an elimination, at least in part, of active and harmful molecules such as toxins, fertilizers, pesticides or chemical warfare vectors (in the case of CBRN defense, for instance) present on a surface or an object.

The cleaning assembly 8 includes a gas supply 10 and a non-thermal cleaning device 12 (hereinafter referred to as "cleaning device") fluidly connected to the gas supply 10.

The cleaning device 12 is configured to receive an object 14 to be cleaned, and to perform cleaning of said object 14.

The object 14 may be a reusable medical device such as, but not limited to, a surgical tool, a robotic arm or part thereof, an endoscope or part thereof, or a single use medical device such as, but not limited to, an implant, a tailor-made surgical tool, single use endoscope parts, and so on.

Moreover, the gas supply 10 is configured to provide a gas to the cleaning device 12, and more specifically a gas that is suitable for the generation of a non-thermal plasma within the cleaning device 12.

Preferably, the gas provided by the gas supply is air. Alternatively, the gas provided by the gas supply 10 includes nitrogen, oxygen, argon, helium and/or any mixture thereof. The use of such chemical species is advantageous, since they are, for the most part, harmless to users, and do not leave hazardous reactive chemical residues after use. This is particularly beneficial, since known sterilization techniques using chemical agents such as ethylene oxide or hydrogen peroxide are known for leaving residues after use, thereby causing potential harm to the patients. This has, for instance, led to a ban of the use of ethylene oxide in the EU, and limitations regarding its use in the USA.

Moreover, gases such as air, nitrogen, oxygen, argon, helium are conventionally available in a hospital environment, at a reasonable cost, thereby limiting the costs of sterilization.

Cleaning Device 12

As mentioned above, the cleaning device 12 is configured to receive the object 14, and to achieve its cleaning.

The cleaning device 12 includes an enclosure 16, a radio-wave source 18, such as a radiofrequency generator or the like, and a controller 22. Preferably, the cleaning device 12 further includes a pump 24.

The enclosure 16 is intended to receive at least one object 14. Moreover, the enclosure 16 is fluidly coupled to the pump 24. The enclosure 16 is also coupled to the radio-wave source 18. Furthermore, the controller 22 is configured to control operation of the radio-wave source 18 and, preferably, of the enclosure 16 and/or the pump 24.

By “radio-wave”, it is meant an electromagnetic wave having a frequency lower than 300 GHz.

Enclosure 16

The enclosure 16 comprises inner walls 26 that define an internal cavity 28 for receiving the object 14. The enclosure 16 also includes a door (not shown) for accessing the internal cavity 28, for instance for loading the object 14. The enclosure 16 further includes an input port 30 and an output port 32 for allowing gas to flow into and out of the internal cavity 28.

The enclosure 16 may further comprise at least one sensor 34 configured to perform a measurement of a predetermined physical property within the internal cavity 28.

Advantageously, the inner walls 26 are made, at least in part, in a material that is compatible with high vacuum process, and preferably resistant to plasma, such as aluminum or stainless steel.

By “material resistant to plasma”, it is meant, in the context of the invention, a material that is not degraded by plasma, i.e., that does not lose mass and/or thickness, and/or that is not oxidized, to such extend that its physical and/or mechanical properties are affected over a predetermined total period of use of the cleaning device 12.

Preferably, dimensions of the inner walls 26 are chosen so that they are able to withstand, without irreversible deformation, a pressure in the internal cavity 28 that is lower than 4000 Pa, preferably comprised between $0.5\times10^{-6}$ Pa and 400 Pa, i.e., ranging from low to high vacuum.

Even more preferably, the enclosure 16 is arranged so that, when the door is closed during a cleaning step disclosed more in details in the following of the description, fluids can only flow into and out of the internal cavity 28 through the input port 30 and/or the output port 32.

Each of the input port 30 and the output port 32 may have an open and a closed position to, respectively, allow or prevent a flow of gas between the internal cavity 28 and the external environment of the enclosure 16.

Each sensor 34 is configured to output a sensing signal representative of a current value of a corresponding physical property within the internal cavity 28. For instance, such physical property is a pressure or a temperature within the internal cavity 28.

Radio-Wave Source 18

The radio-wave source 18 is configured to output an electromagnetic wave 36, and more specifically a radio wave.

More precisely, the radio-wave source 18 has an active state and an inactive state. In the active state, the radio-wave source 18 outputs the electromagnetic wave 36. Conversely, in the inactive state, the radio-wave source 18 does not output any electromagnetic wave.

More precisely, the radio-wave source 18 is coupled to the enclosure 16 so that, in the active state, the electromagnetic wave 36 propagates in the enclosure 16, and more specifically in the internal cavity 28.

The electromagnetic wave 36 has a frequency in the radio wave range or the microwave range.

Advantageously, the radio-wave source 18 is configured so that the electromagnetic wave 36 has a frequency included in one or more of: the LF band (or “low frequency band”, ranging between 30 kHz and 300 kHz), the MF band (or “medium frequency band”, ranging between 300 kHz and 3 MHz) and the HF and VHF band (or “high frequency band”, ranging between 3 MHz and 30 MHz and 30 MHz to 300 MHz).

Such frequency ranges provide several advantages in comparison to other frequency ranges of the spectrum. Indeed, electromagnetic waves in the UHF band (“ultra-high frequency band”, ranging between from 300 MHz to 3 GHz) would have wavelengths close to the characteristic wavelength of the materials placed in the enclosure. Consequently, the energy transfer from the electromagnetic wave to the gas in the enclosure would result in quick heating of the materials placed in the enclosure potentially affecting their physical characteristics and integrity.

Furthermore, the UHF band is classically employed for radio communications/telecommunications, leading to a very high risk of interference with other devices, and potentially causing electromagnetic compatibility problems, especially in a medical environment.

For example, the radio-wave source 18 is configured so that the electromagnetic wave 36 has a frequency belonging to a range compatible with standard ISM (Industrial, Scientific and Medical) equipment, which uses frequency bands harmonized by the ITU (International Telecommunication Union). Such preferred frequency ranges are:

6.78 MHz±15 kHz (i.e., 6.765 MHz to 6.795 MHz);

13.56 MHz±7 kHz (i.e., 13.553 MHz to 13.567 MHz); and 27.12 MHz±163 kHz (i.e., 26.957 MHz to 27.283 MHz).

Such frequency ranges promote electromagnetic compatibility in a medical environment.

Alternatively, or in addition, especially for objects 14 that are not sensitive to interferences, the radio-wave source 18 is configured so that the electromagnetic wave 36 has a frequency included in the microwave range, that is to say between 300 MHz and 300 GHz. For instance, the radio-wave source 18 is configured so that the electromagnetic wave 36 has a frequency comprised between 1 GHz and 5 GHz, preferably between 2 GHz and 3 GHz, for instance equal to 2.45 GHz.

The location of the radio-wave source 18 relative to the enclosure 16 and the output power of the radio-wave source 18 are chosen so that, when suitable pressure and gas composition are achieved in the internal cavity 28, controlling the radio-wave source 18 so that it is in its active state results in the ignition of a non-thermal plasma in the internal cavity 28.

Controller 22

As mentioned previously, the controller 22 is configured to control operation of the radio-wave source 18.

More precisely, the controller 22 is configured to successively perform, during a cleaning step for cleaning the object 14, at least two, preferably, at least three, non-thermal plasma generation cycles. In this case, the controller 22 is configured to control, during each non-thermal plasma generation cycle, the radio-wave source 18 to:

- be in the active state during a first predetermined duration; and
- be in the inactive state during a second predetermined duration following the first predetermined duration.

Each of the first predetermined duration and the second predetermined duration is strictly greater than zero.

Consequently, provided that suitable pressure and gas composition are achieved in the internal cavity 28, a non-thermal plasma is generated in the enclosure 16, thereby leading to a cleaning of the object 14.

Moreover, the input port 30 is in an open state during the second predetermined duration, in order to allow a flow of gas from the gas supply 10 to the enclosure 16, and more precisely to the internal cavity 28. Possibly, the input port 30 may also be in the open state during the first predetermined duration or a part thereof, as the radio-wave source is in the active state.

For instance, the controller 22 is configured to control the position of the input port 30 so that said input port 30 is in the open position during the second predetermined duration and possibly at least a part of the first determined duration. Alternatively, the input port 30 does not require control from the controller 22, and is always in an open position.

Thanks to the invention, a cleaning that is far more efficient than that associated to known non-thermal plasma cleaning devices is achieved. Indeed, the inventors have discovered that the reaction kinetics involved in the generation of the plasma are such that the chemical species that contribute the most to the degradation of undesired chemicals and/or pathogens (i.e., radicals and/or molecules in an excited state), hereinafter called “reactants of interest”, are present in a very small minority, in the steady-state, compared to other less reactive species. On the contrary, the fraction of the reactants of interest is significantly higher in the transient state.

Consequently, by performing a plurality of such non-thermal plasma generation cycles, and by allowing a flow of gas from the gas supply to the enclosure at least during the predetermined second duration of each non-thermal plasma generation cycle, the reactants of interest that appear when the plasma is ignited are regenerated, thereby providing enhanced cleaning performances to the cleaning device according to the invention.

Furthermore, the ignition of the plasma within the internal cavity 28 itself leads to results that are far better than those achieved with known devices that perform cleaning using an afterglow discharge (also referred-to as “plasma beam cleaning”).

Indeed, when performing plasma beam cleaning, a flow of gas goes through a discharge region, wherein the plasma is ignited. Said plasma is then transported to the object to be cleaned, which is located at a distance from the discharge region. However, the inventors have discovered that the aforementioned reactants of interest include reactants having a very short lifespan. Consequently, when the plasma reaches the object to be cleaned, said reactants of interest have almost completely undergone a chemical change, and thereby lose their efficiency. On the contrary, thanks to the invention, the plasma is ignited around the object 14 to be cleaned, and the problem resulting from the transport of the plasma is overcome.

Preferably, for each non-thermal plasma generation cycle, the first predetermined duration is less than 5 minutes, preferably less than 3 minutes, advantageously less than 2 minutes, for instance less than 1 minute.

Indeed, as mentioned previously, the reactants of interest is a mix including reactants having a short lifetime, and increasing the first duration beyond a certain amount of time (typically, the lifetime of the part of the reactants of interest) would not result in significant advantages.

Figure 3:
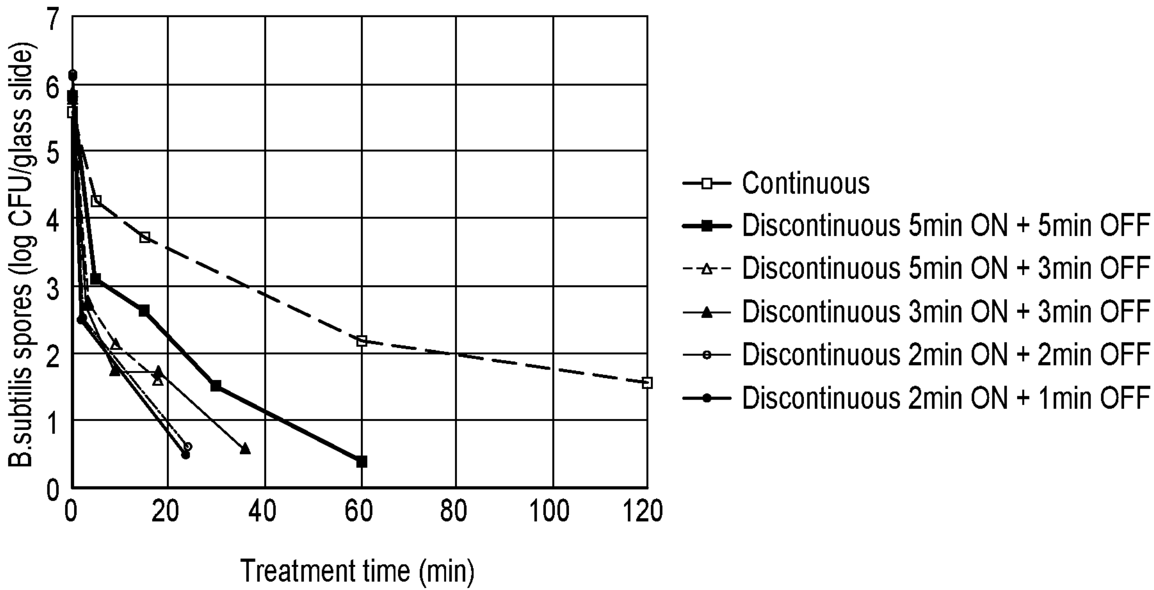
FIG. 3 is a graph showing the evolution, as a function of time, of the number (in logarithmic scale) of spores on a surface cleaned using the cleaning assembly of FIG. 2, with various durations of exposure to a non-thermal plasma.

This can be easily understood from FIG. 3 which illustrates the evolution, as a function of time, of the number (in logarithmic scale) of spores (*Bacillus subtilis* spores) with various durations of exposure to a non-thermal plasma, namely:

- a continuous exposure to a non-thermal plasma,
- a discontinuous exposure to a non-thermal plasma, in which the radio-wave source is “ON”, namely in the active state, for a first predetermined duration of 5 minutes, and “OFF”, namely in the inactive state, for a second duration of 5 minutes,
- a discontinuous exposure to a non-thermal plasma, in which the radio-wave source is “ON” for a first predetermined duration of 5 minutes, and “OFF” for a second duration of 3 minutes,
- a discontinuous exposure to a non-thermal plasma, in which the radio-wave source is “ON” for a first predetermined duration of 3 minutes, and “OFF” for a second duration of 3 minutes,
- a discontinuous exposure to a non-thermal plasma, in which the radio-wave source is “ON” for a first predetermined duration of 2 minutes, and “OFF” for a second duration of 2 minutes,
- a discontinuous exposure to a non-thermal plasma, in which the radio-wave source is “ON” for a first predetermined duration of 2 minutes, and “OFF” for a second duration of 1 minute.

It can be seen that increasing the duration of exposure to a non-thermal plasma (i.e., increasing the first predetermined duration) actually increases the amount of time required to achieve a division by $10^6$ of the number of spores on the object 14.

Figure 4:
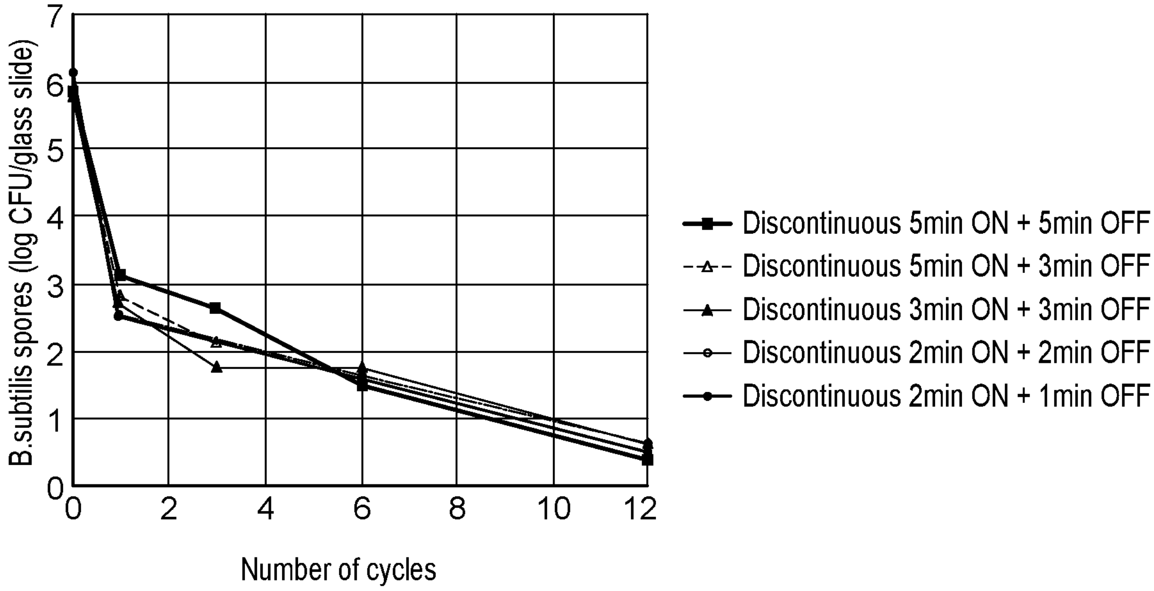
FIG. 4 is a graph showing the evolution, as a function of non-thermal plasma generation cycles, of the number (in logarithmic scale) of spores on a surface cleaned using the cleaning assembly of FIG. 2, with various durations of exposure to the non-thermal plasma.

More specifically, and as shown on FIG. 4 showing the evolution, as a function of non-thermal plasma generation cycles, of the number (in logarithmic scale) of spores (*Bacillus subtilis* spores) with the aforementioned durations of exposure to the non-thermal plasma, provided that the first duration is at least equal to the lifetime of the reactants of interest, it is actually the number of cycles that has an influence on the cleaning efficiency. In other words, the cleaning efficiency depends on the amount of time that the object 14 is exposed to the reactants of interest.

Preferably, the controller 22 is configured to successively perform, during the cleaning step, at least two, especially at least three non-thermal plasma generation cycles, and preferably at least five non-thermal plasma generation cycles.

Moreover, for each non-thermal plasma generation cycle, the second predetermined duration is less than 5 minutes, preferably less than 3 minutes, advantageously less than 2 minutes, for instance less than 30 seconds.

Indeed, the second duration should be as short as possible since, during the second duration, cleaning is not achieved due to the absence of plasma. This results from the fact that the plasma within the enclosure 16 rapidly goes off (a few seconds, generally less than 5 seconds) once the radio-wave source 18 is switched to its inactive state.

Advantageously, the input port 30 is sized so that, during said predetermined second duration, a predetermined amount of gas is injected in the enclosure 16, and more specifically in the internal cavity 28. As an example, said injected amount of gas is at least equal to the amount of gas present in the internal cavity 28 during the first duration, preferably at least equal to three times that amount, for instance at least equal to ten times said amount. In other words, the input port 30 is sized so that, during the second predetermined duration, the gases in the internal cavity 28 are renewed before the next non-thermal plasma generation cycle.

The flow rate of the pump 24 may also be optimized in conjunction to the input port 30 so that, during the second predetermined duration, the gases in the internal cavity 28 are renewed before the next non-thermal plasma generation cycle.

For instance, with a flow rate of dioxygen of 1 scmm (Standard Cubic Centimeters per Minute), a pressure in the internal cavity of $10^{-4}$ mbar (millibar), a temperature of the gas at the input port of 273.15 K (kelvin), and an internal cavity 28 having a volume of 10 L, the second predetermined duration can be as short as 5 seconds.

As mentioned previously, the controller 22 is also configured to operate the pump 24. More precisely, the controller 22 is configured to control the pump 24 so that, during at least one non-thermal plasma generation cycle, the pressure within the enclosure is below a predetermined threshold.

Preferably, the predetermined threshold is lower than 4000 Pa, preferably comprised between $0.5\times10^{-6}$ Pa and 400 Pa.

Advantageously, the controller 22 is configured to operate the pump 24 based on the sensing signal output by one or several sensor(s) 34, and more precisely on a pressure within the enclosure 16 (that is to say, in the internal volume 28) derived from the sensing signal.

Advantageously, the controller 22 is configured to operate the radio-wave source 18 based on the sensing signal output by one or several sensor(s) 34, and more precisely on a temperature of the object 14 derived from the sensing signal. For instance, the controller 22 is configured to control the radio-wave source 18 so that it is in its inactive state if the temperature of the object 14 is greater than a predetermined maximum value. Consequently, a heat-related degradation of the object 14 is prevented.

Operation

Operation of the cleaning assembly 8 will now be described.

During an initialization step, the cleaning device 12 is connected to the gas supply 10. Moreover, the controller 22 is configured: for instance, the first duration, the second duration are stored in the controller. The controller 22 may also be configured to store the type of gas provided by the gas supply, and/or the number of non-thermal plasma generation cycles that are to be performed during the cleaning step, and/or the measurements of the critical parameters of the cycle for process control, reglementary and safety purposes including but not limited to enclosure pressure, gas flow, radio wave power.

Then, during an initial step, at least one object 14 to be cleaned is arranged in the enclosure 16, and more precisely in the internal cavity 28 of the enclosure 16.

The enclosure is closed and, preferably, the pressure within the enclosure 16 (i.e., in the internal cavity 28) is brought below the predetermined threshold, for instance using the optional pump 24 connected to the output port 32 of the enclosure 16.

Then, during the cleaning step, the controller 22 successively performs at least two, preferably at least three non-thermal plasma generation cycles, for instance based on the type of gas provided by the gas supply 10, and/or the previously stored number of non-thermal plasma generation cycles that are to be performed.

As mentioned previously, during each non-thermal plasma generation cycle, the controller 22 controls the radio-wave source 18 to:

be in the active state during the first predetermined duration, thereby generating a non-thermal plasma in the enclosure 16; and be in the inactive state during the second predetermined duration following the first predetermined duration.

Furthermore, during the second predetermined duration, a flow of gas is injected in the enclosure 16. In other words, during the second predetermined duration, a position of the input port 30 allows gas to flow from the gas supply to the enclosure 16. Possibly, a flow of gas may also be injected in the enclosure 16 during a part or all the first predetermined duration.

Then, during a storing step, each cleaned object 14 is stored in a corresponding packaging.

Figure 5:
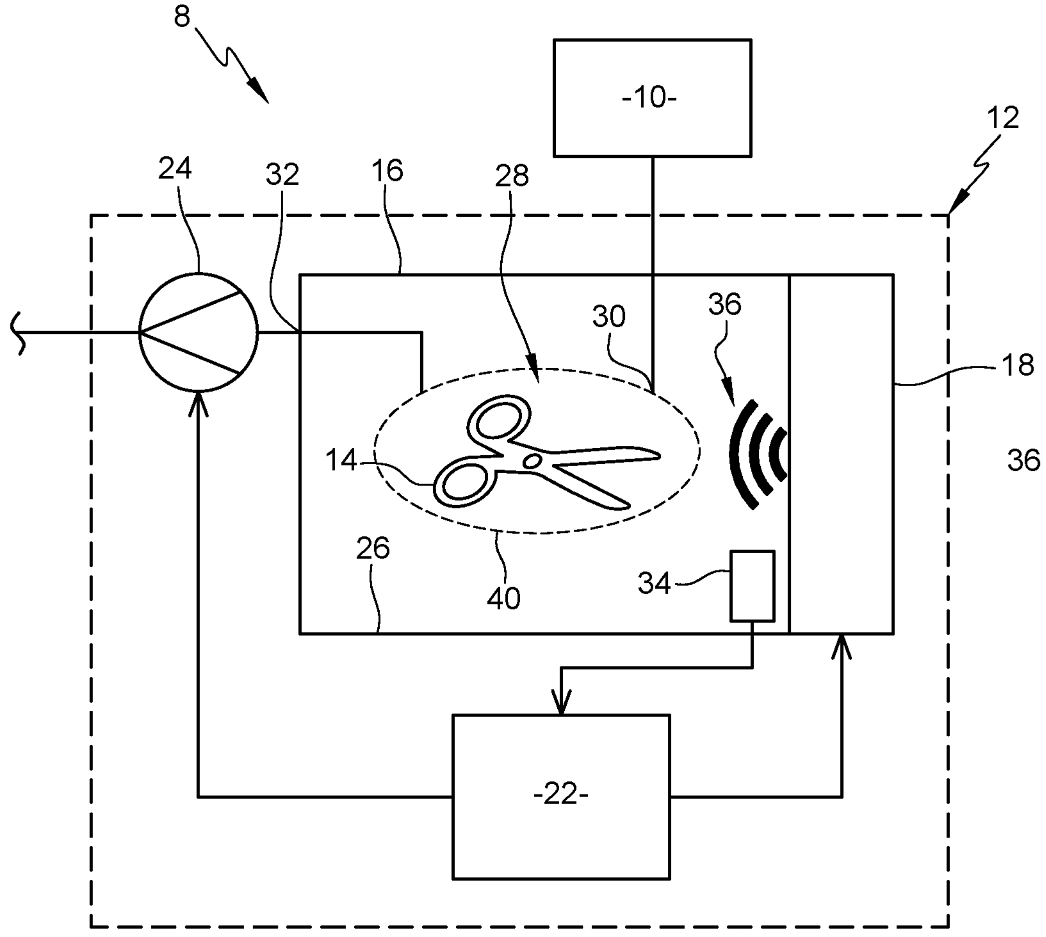
FIG. 5 is a schematic representation of a second embodiment of a cleaning assembly according to the invention.

Alternatively, the object 14 to be cleaned is provided in a corresponding packaging 40, as shown on FIG. 5.

In this case, the packaging 40 can be considered as the enclosure, and is provided with an input port 42 connectable to the gas supply 10, and an output port 44 connectable to the outside environment, for instance through the pump 24.

For the sake of convenience, a frame 44 is provided, coupled to the radio-wave source 18 so that, when packaging 40 is arranged in the frame 44 and the radio-wave source 18 is in its active state, the electromagnetic wave propagates in the packaging 40, thereby allowing the ignition of a non-thermal plasma.

In this case, after the step of cleaning, the packaging containing the cleaned object 14 is removed from the frame and sealed, without the need to arrange the object 14 in another sealable bag for storing purposes.

The invention claimed is:

1. A non-thermal plasma cleaning device including:

an enclosure for receiving at least one object to be cleaned, the enclosure including an input port for fluidly connecting the enclosure to a gas supply;

a radio-wave source having an active state wherein the radio-wave source outputs an electromagnetic wave and an inactive state wherein the radio-wave source does not output the electromagnetic wave, the electromagnetic wave having a frequency in the radio wave range or the microwave range, the radio-wave source being coupled to the enclosure so that, in the active state, the electromagnetic wave propagates in the enclosure;

a controller configured to successively perform, during a cleaning step, at least two non-thermal plasma generation cycles, each non-thermal plasma generation cycle comprising:

controlling the radio-wave source to be in the active state during a first predetermined duration, thereby generating a non-thermal plasma in the enclosure; and following the first predetermined duration, controlling the radio-wave source to be in the inactive state during a second predetermined duration, the input port being in an open state at least during the second predetermined duration to allow a flow of gas into the enclosure, each of the first predetermined duration and the second predetermined duration being strictly greater than zero.

2. The non-thermal plasma cleaning device according to claim 1, further including a pump fluidly connected to the enclosure, the controller being configured to operate the pump so that, during at least one non-thermal plasma generation cycle, a pressure within the enclosure is below a predetermined threshold.

3. The non-thermal plasma cleaning device according to claim 2, wherein the predetermined threshold is lower than 4000 Pa.

4. The non-thermal plasma cleaning device according to claim 1, wherein the radio-wave source is configured so that the electromagnetic wave has a frequency:

comprised in an interval ranging from 30 kHz to 300 MHz; and/or comprised between 1 GHz and 5 GHz.

5. The non-thermal plasma cleaning device according to claim 1, wherein the first predetermined duration is less than 5 minutes.

6. The non-thermal plasma cleaning device according to claim 1, wherein the second predetermined duration is less than 5 minutes.

7. The non-thermal plasma cleaning device according to claim 1, wherein the controller is configured to successively perform, during the cleaning step, at least five non-thermal plasma generation cycles.

8. The non-thermal plasma cleaning device according to claim 1, further including at least one sensor configured to output a sensing signal representative of a temperature within the enclosure, the controller being further configured to control the radio-wave source to be in the inactive state if the temperature determined based on the sensing signal is greater than a predetermined maximum value.

9. A cleaning assembly including the gas supply and the non-thermal plasma cleaning device according to claim 1, the gas supply being fluidly connected to the input port of the enclosure to provide gas to the enclosure of the non-thermal plasma cleaning device.

10. The cleaning assembly according to claim 9, wherein the gas is air, or includes at least one of: nitrogen, oxygen, argon and helium.

11. The cleaning assembly according to claim 9, wherein the gas supply and the input port of the enclosure are sized so that, during the second predetermined duration, a predetermined amount of gas is injected in the enclosure.

* * * * *